United States Patent
Doyle et al.

(10) Patent No.: US 6,805,664 B2
(45) Date of Patent: Oct. 19, 2004

(54) CLUTCH FOR STABILIZING AND ADJUSTING A PROBE IN LAPAROSCOPIC SURGERY

(75) Inventors: Mark Doyle, San Diego, CA (US); Jimmy Caputo, Carlsbad, CA (US)

(73) Assignee: Tiva Medical, Inc., Carlsbad, CA (US)

(*) Notice: Subject to any disclaimer, the term of this patent is extended or adjusted under 35 U.S.C. 154(b) by 155 days.

(21) Appl. No.: 10/211,016

(22) Filed: Jul. 31, 2002

(65) Prior Publication Data

US 2004/0024383 A1 Feb. 5, 2004

(51) Int. Cl.[7] .................................................. A61B 1/00
(52) U.S. Cl. ........................................ 600/102; 600/114
(58) Field of Search .............................. 600/102, 114; 606/1, 130

(56) References Cited

U.S. PATENT DOCUMENTS

| | | | |
|---|---|---|---|
| 3,822,697 A | * | 7/1974 | Komiya ..................... 600/114 |
| 5,649,956 A | | 7/1997 | Jensen et al. |
| 5,658,272 A | | 8/1997 | Hasson |
| 5,697,939 A | | 12/1997 | Kubota et al. |
| 5,776,144 A | | 7/1998 | Leysieffer et al. |
| 5,797,835 A | | 8/1998 | Green |
| 5,810,880 A | | 9/1998 | Jensen et al. |
| 5,824,007 A | | 10/1998 | Faraz et al. |
| 5,957,423 A | | 9/1999 | Kronner |
| 6,080,181 A | | 6/2000 | Jensen et al. |
| 6,306,146 B1 | | 10/2001 | Dinkler |

* cited by examiner

Primary Examiner—Beverly M. Flanagan
(74) Attorney, Agent, or Firm—Knobbe Martens Olson & Bear LLP

(57) ABSTRACT

Disclosed is a clutch for a surgical device comprising a housing having an interior wall defining a hollow interior; a shaft, the shaft being capable of moving axially and rotationally within the hollow interior of the housing; at least one clutch element connected with the shaft; and an activator; where the surgical device is a laparoscopic surgical tool.

21 Claims, 3 Drawing Sheets

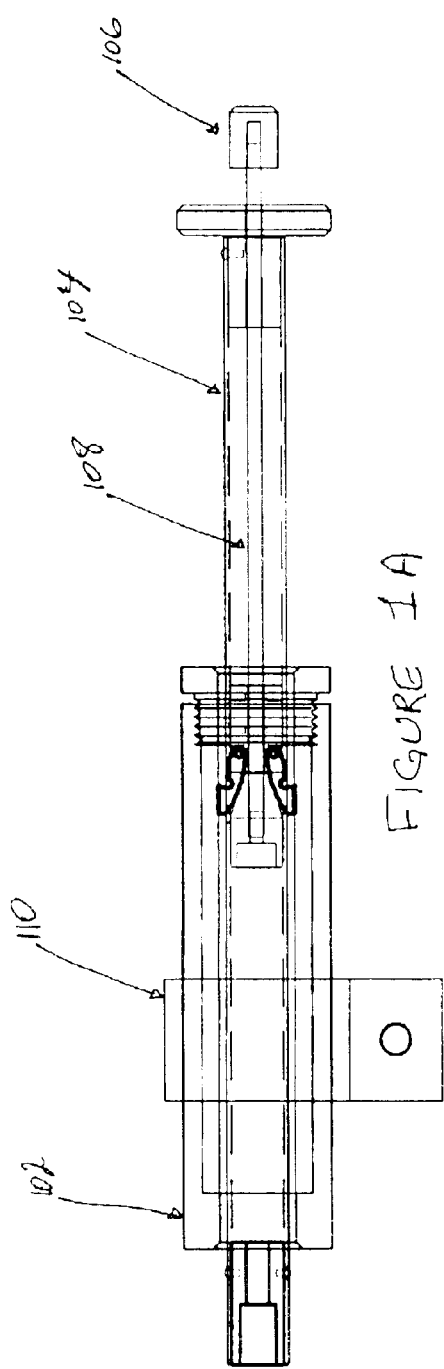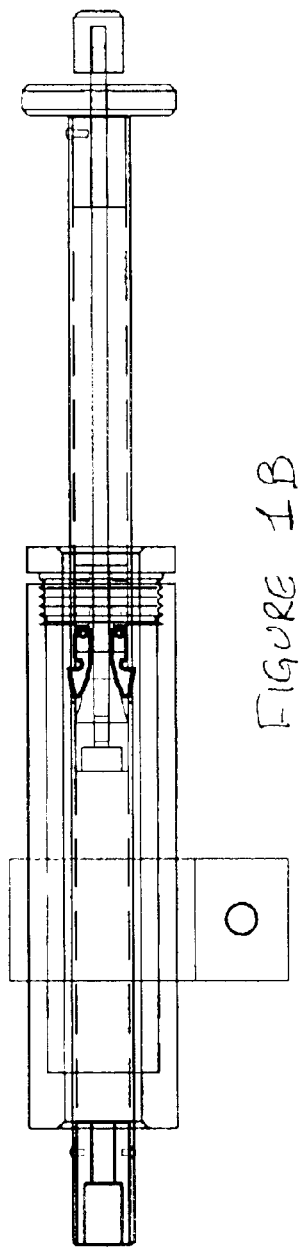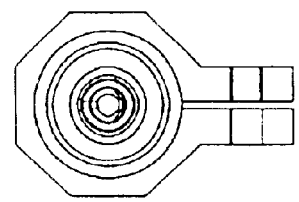

US 6,805,664 B2

CLUTCH FOR STABILIZING AND ADJUSTING A PROBE IN LAPAROSCOPIC SURGERY

FIELD OF THE INVENTION

The present invention relates to a clutch device to be used for coarse adjustment of the position of a device. In one embodiment, the clutch is used to stabilize and adjust the position of a laparoscopic surgical tool during laparoscopic surgery.

BACKGROUND OF THE INVENTION

Current laparoscopic surgical tools are limited in accessibility of certain regions of the human body. Existing tools can perform invasive surgery without making a substantial incision, but these tools are incapable of bending within the body to reach, for example, the backside of the human heart. In addition, after being placed in the desired position, current tools are capable of very small movements at the tip of the tool. If the surgeon desires to move the tip a substantial distance, or reposition the tool, the surgeon must move the entire tool, often with both hands, at which point, the surgeon will not be able to operate the tip of the tool during the movement, and the tool will not be in a stable position during the movement.

Consequently, there exists a need in the art to provide a device by which the surgeon can reposition the surgical tool with only one hand while still operating the tip of the tool with the other hand, and while the device remains stable during and after the movement.

SUMMARY OF THE INVENTION

Disclosed is a clutch for adjusting the position of a device, comprising a housing having an interior wall defining a hollow interior; a shaft being capable of moving axially and rotationally within the hollow interior of the housing; at least one clutch element connected with the shaft; and an activator; whereby when the activator is disengaged the clutch element is in contact with the interior wall of the housing, preventing the movement of the shaft relative to the housing, and when the activator is engaged, the clutch element is not in contact with the interior wall of the housing, allowing for the movement of the shaft relative to the housing; where the device is connected to the shaft and the movement of the shaft relative to the housing moves at least a distal end of the device.

BRIEF DESCRIPTION OF THE DRAWINGS

The features, objects and advantages of the present invention will become more apparent from the detailed description set forth below when taken in conjunction with the drawings in which like references identify correspondingly throughout, and wherein:

FIG. 1 is an overview of one embodiment of the invention. FIG. 1A shows the top view of one embodiment when the clutch element 202 is in contact with the interior wall of the housing 102, while FIG. 1B shows the top view of one embodiment when the clutch element 202 is not in contact with the interior wall of the housing 102. FIG. 1C is the front view of the device.

DETAILED DESCRIPTION OF THE PREFERRED EMBODIMENTS

Figure 2:
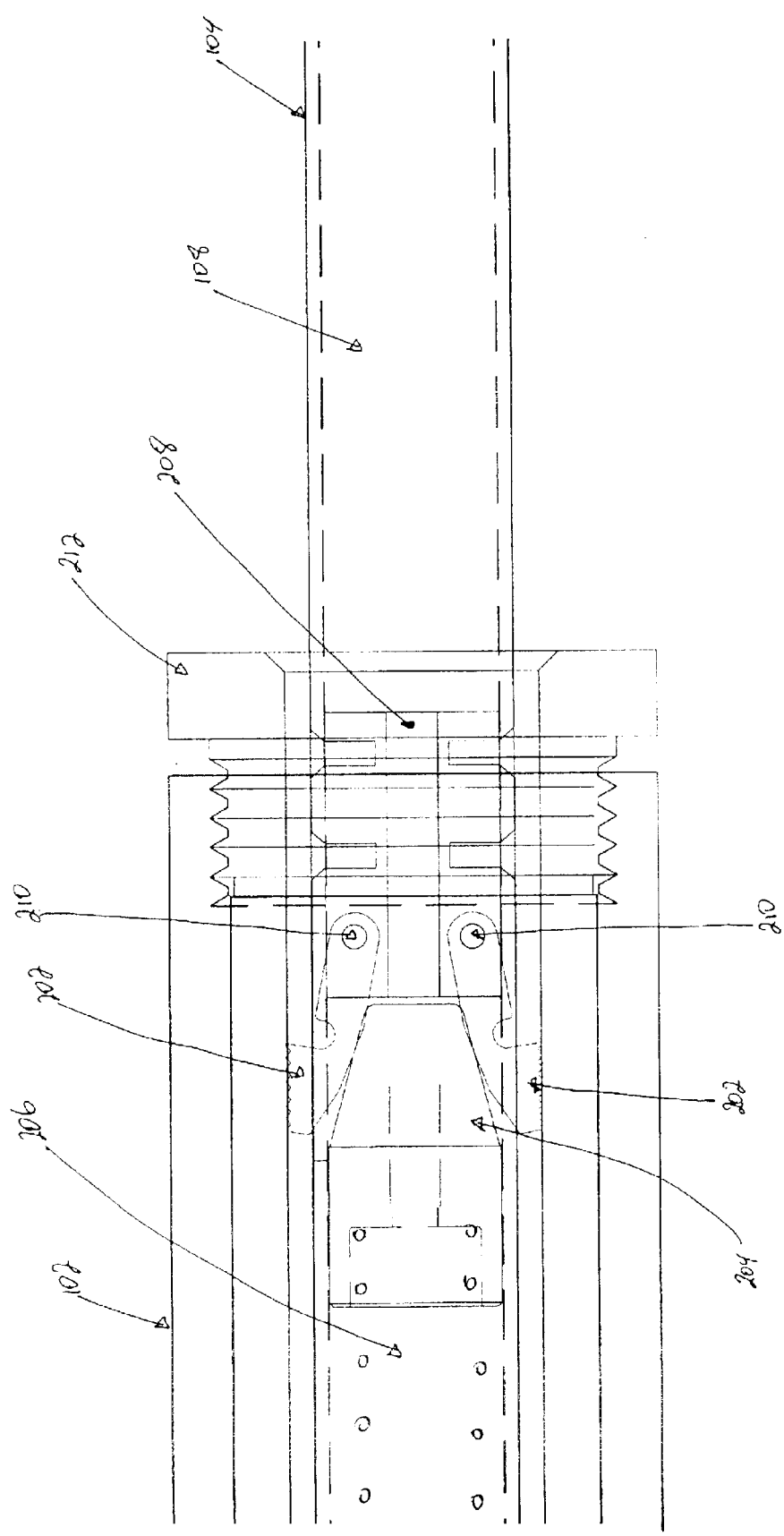
FIG. 2 is an expanded view of FIG. 1A, showing the proximal end of the housing 102 along with two clutch elements 202 in contact with the interior wall of the housing 102.

The device of the present invention is a hand-actuated clutch, which is mounted within a translating or rotating shaft. This device can be used to coarsely adjust the position of an instrument, which instrument may be connected to the device of the present invention. In certain embodiments, the instrument attached to the device of the present invention is a laparoscopic surgical tool, such as the one described in the International Publication No. WO 02/07608, published Jan. 31, 2002, by Doyle et al. and entitled "HAND-ACTUATED ARTICULATING SURGICAL TOOL," and U.S. patent application Publication Ser. No. US2002/0111604 A1, published Aug. 15, 2002, by Doyle et al. and entitled "HAND-ACTUATED ARTICULATING SURGICAL TOOL," both of which are incorporated herein by reference in their entirety, including any drawings.

The operators of certain instruments, such as the surgical tool described in the above publications, are capable of adjusting the position of the tip of the instruments finely. However, given the position of the instrument and the delicacy of the environment in which they operate, coarse adjustments of the position of the instrument becomes difficult. In addition, the operator of the instrument may wish to operate the instrument with one hand and adjust the position of the instrument with another. For example, a surgeon may wish to make a cut using a scalpel attached to the tip of a laparoscopic surgical tool, which cut is to be longer than the fine adjustment of the tip of the tool can provide. The surgeon would need to operate the scalpel with one hand and make a coarser adjustment of the position of the tip with another to make the cut.

The device of the present invention provides a clutch apparatus that provides a smooth adjustment of the position of an instrument attached thereto, while providing a stable platform when the adjustment is not being made. In addition, an operator of the device of the present invention can use it to make the necessary adjustments using only one hand. As used herein, the word "instrument" refers to a device, tool, or instrument that is attached to the device of the present invention and whose position or the position of whose tip or whose distal end is being adjusted by the device of the present invention.

Thus, in one of its myriad of uses, the device of the present invention is useful in aiding surgeons during laparoscopic surgery. The laparoscopic surgical tool can be attached to the device of the present invention using a clamp or a similar tool. The device of the present invention will then provide greater stability for the surgical tool to be used. The clutch device can be clamped to a surgical bed-rail, or any other part of a surgical bed, or a table near a surgical bed, during the surgery and thereby stabilize the surgical tool that is attached to the device of the present invention. The device also eliminates the need for the operator of the surgical tool to hold the tool during operation, freeing both hands of the operator.

The clutch device of the present invention can rotate and move longitudinally, thus providing both rotational and axial movements. By providing additional degrees of freedom in adjusting the position of the tip of the instrument, the device can act as a third hand for the operator. The operator can place the tip of the instrument near the area of use, and using the fine adjustments of the instrument itself, the operator can perform the function of the instrument. The operator then can move the tip for a greater distance using the device of the present invention with one hand while still operating the tip of the instrument with another hand. This feature, as well as the ability of the clutch device to hold and support the instrument itself, greatly reduces the operator's fatigue.

In one embodiment, the device of the present invention is used with a hand-actuated laparoscopic surgical tool, which comprises a cannula comprising hydraulic tubings, connecting certain control cylinders of slave cylinders at the distal end of the cannula, and housings for the hydraulic tubings. The distal end of the cannula comprises modular components. The components can be selected from, for example, an extend module, a rotate module, a bend module, and a grasp module. Other modules can also be selected. The cannula is then clamped to the device of the present invention at a point distal to the control portion of the laparoscopic surgical tool, where the control cylinders are located, but proximal to the point of the cannula that is inserted into the patient's body. As described in the International Publication No. WO 02/07608, and U.S. patent application Publication Ser. No. US 2002/0111604 A1, the extend module of the laparoscopic surgical tool can move the tip of the surgical tool for a short distance. In addition, the rotate and bend modules can reposition or adjust the position of the surgical tip to a certain degree. However, without the benefit of the device of the present invention, if the surgeon is required to make a long incision, or if the surgical tip is to be moved a few inches to reach another section of the body to be operated on, the surgeon will have to remove the laparoscopic surgical tool from the patient's body and reinsert it in another location. Or the surgeon will have to carefully and using both hands manipulate the clamps that attach the surgical tool to the bed or other means of support in order to readjust the position of the tip.

However, using the device of the present invention, the surgeon can move or rotate the surgical tip with one hand to a much greater degree. The tip can be moved smoothly and the entire tool remains stable during the adjustment of the position. In addition, the surgeon can still operate the various modules of the laparoscopic surgical device with one hand while adjusting the position using the clutch device of the present invention with another hand.

As used herein, the term "proximal" refers to the portion of the device that is closest to the operator. The most proximal section of the device is the activator 106 shown in FIG. 1. The term "distal" refers to the portion of the device furthest away from the operator and the activator 106.

Certain embodiments of the invention will now be described in detail with reference to the figures.

Housing

Figure 3:
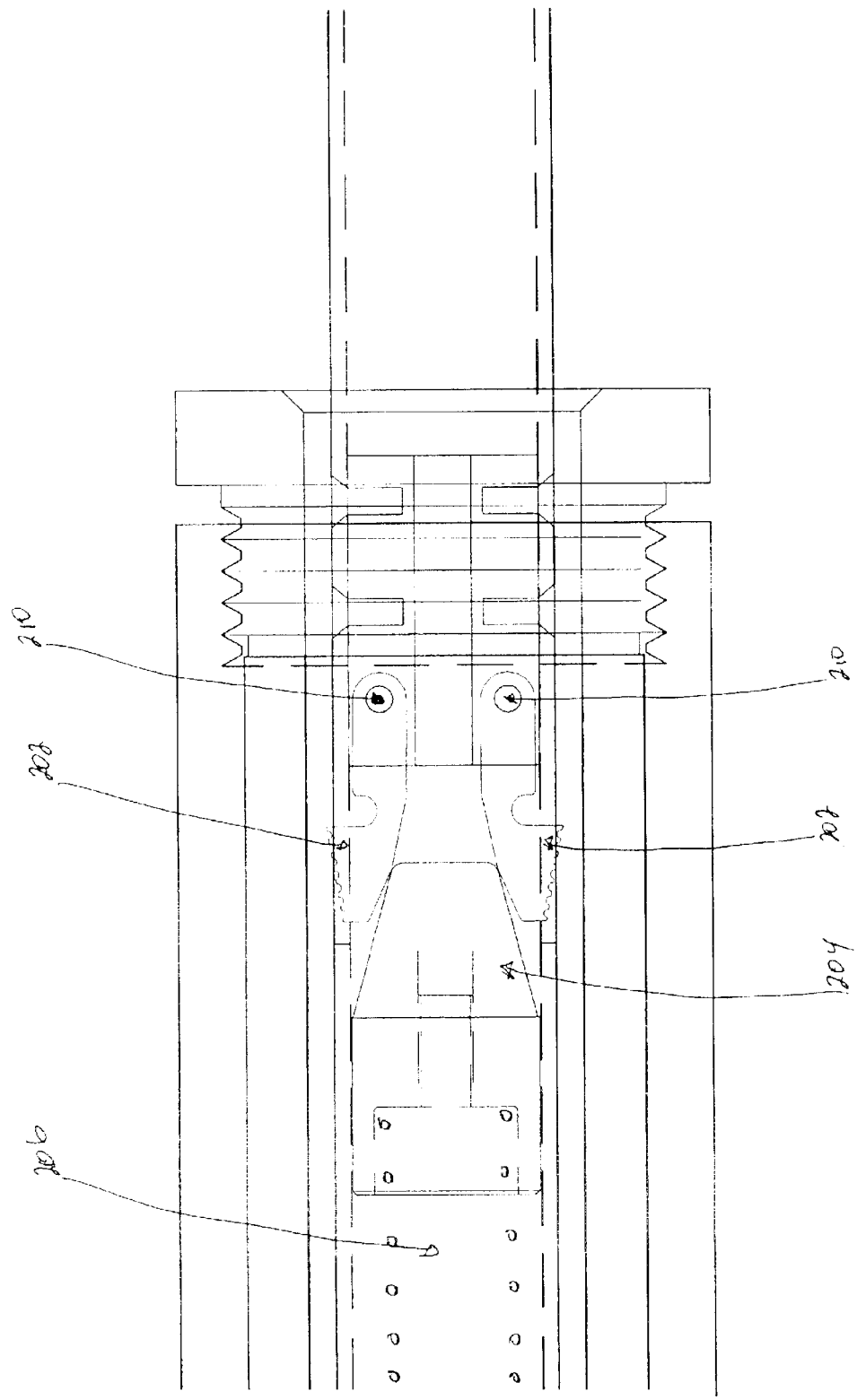
FIG. 3 is an expanded view of FIG. 1B, showing the proximal end of the housing 102 along with two clutch elements 202 not in contact with the interior wall of the housing 102.

FIGS. 1, 2, and 3 show a clutch apparatus 100 according to the present invention. The apparatus comprises a housing 102. The housing 102 is preferably cylindrical; however, it may be of any shape commensurate with the objectives of the apparatus. The housing 102, thus, may be cylindrical, cubical, or any other shape whose cross section defines a circle, ellipse, or a polyhedron. Common polyhedrons include, but are not limited to, triangles, squares, rectangles, parallelograms, pentagons, hexagons, heptagons, octagons, trapezoids, etc., which may have sides that are of the same or different lengths. The housing 102 may have an outer body of varying, or constant, diameters. Thus, the outer body of the housing 102 may form ridges that make the housing more convenient to handle or to attach to other apparati, such as a clamp.

The housing 102 can be made of a number of different materials. Some suitable materials that can form the housing 102 include, but are not limited to, wood, stainless steel, aluminum, ceramic, a polymer, such as plastic, and rubber. If the housing 102 is made of metal, the metal may be in pure form or be present as an alloy.

The housing 102 comprises a hollow interior. The interior of the housing 102 is of such shape and size to accommodate a shaft 104 to slide therethrough. Preferably, the interior of the housing 102 is cylindrical, i.e., the cross section of the interior defines a circle. However, other embodiments where the cross section of the interior is of a different shape, such as an ellipse or a polyhedron, are also contemplated. The shape of the cross section of the interior of the housing 102 is preferably the same shape as the shape of the cross section of the shaft 104.

In some embodiments, the surface of the wall of the interior of the housing 102 is unlined, and therefore, is of the same material as the housing 102 itself. In other embodiments, the interior surface of housing 102 is lined. The lining may be soft or textured. In some embodiments, the lining is made of material into which the clutch element 202 can penetrate. The lining may be made of rubber, low durometer polymer, such as placticized PVC or polyurethane, textured high durometer polymer or elastomer, such as polyacetals or polycarbonates, and textured metal. In other embodiments, the lining provides small features that correspond to any features on the clutch element 202, thereby securing the clutch element 202 against the interior wall of the housing 102.

The proximal end of the housing 102 may be capped by a cap 212. Once the cap 212 is in place, the shaft 104 cannot be removed from the housing 102. The cap 212 may be a screw-cap or it may be a push-cap. In other embodiments, the shaft 104 may be secured to the housing 102 by a retaining ring.

The housing 102 may be affixed to a stationary object by, for example, a clamp 110. The stationary object may be a surgical bed, bed rail, a table near a surgical bed, a cart, or the like. The stationary object may also be a positioning arm, to which the cannula of a laparoscopic surgical tool is attached.

The instrument, whose position is coarsely adjusted by the device of the present invention, e.g., the cannula of a laparoscopic surgical device, is capable of being attached to shaft 104. In some embodiments, the instrument is attached to the shaft 104, for example by using a clamp. In other embodiments, the instrument, which may be a laparoscopic surgical tool, such as the one described in the International Publication No. WO 02/07608, and U.S. patent application Publication Ser. No. US2002/0111604 A1, may pass through the shaft 104.

Clutch Element

The device of the present invention further comprises at least one clutch element 202. At its proximal end, the clutch element 202 is attached to a pin 210, around which the clutch element 202 is capable of pivoting. The pin 210 and the proximal end of the clutch element 202 are within the shaft 104. When the clutch element 202 pivots about the pin 210, the distal end of the clutch element 202 protrudes out of the shaft 104.

The distal end of the clutch element 202 can be in contact with the interior wall of the housing 102. When there is such contact, the shaft 104 is locked within the housing 102. The distal end of the clutch element 202 may be a flat surface, a sharp point, a ridged surface, or a combination thereof. Thus, the distal end of the clutch element 202 is of such shape and size to provide enough interference with the interior wall of the housing 102 to prevent the shaft from rotating or sliding within the housing.

In certain embodiments, when the activator 106 is engaged, the clutch element 202 collapses naturally away from the interior wall of the housing 102. In other embodiments, when the activator 106 is engaged, the clutch element 202 is deflected away from the interior wall of the housing 102 using mechanical means, e.g., a spring or a spring-loaded lever. In still other embodiments, when the activator 106 is engaged, the clutch element 202 is deflected away form the interior wall of the housing 102 using electrical means, e.g., an electromagnet.

Activator

The shaft 104 comprises an activator 106. In some embodiments, the activator 106 is located at the proximal end of the shaft 104. In other embodiments, the activator 106 is located elsewhere on the shaft 104, for example, on the side. Preferably, the activator 106 is located in such a location where an operator of the device of the present invention can use the activator and simultaneously slide or rotate the shaft 104 through the housing 102 with only one hand.

In certain embodiments the activator 106 is capable of exerting mechanical force that can be translated towards the distal part of the shaft 104, thereby causing cam 204 to move. In some of these embodiments the activator 106 is a button, while in other embodiments the activator 106 is a lever. In still other embodiments, the activator 106 is a switch than can turn an electrical current on or off.

As discussed below in greater detail, when activator 106 is disengaged, the distal end of clutch element 202 protrudes out of shaft 104 and is in contact with the interior wall of the housing 102. The contact between the clutch element 202 and the interior wall of the housing 102 prevents shaft 104 from sliding or rotating within the housing 102, and therefore, is locked to the housing 102 and immobilized. The contact between the clutch element 202 and the interior wall of the housing 102 may be frictional contact or interference contact.

When activator 106 is engaged, the distal end of clutch element 202 is free to pivot about the pin 210. At that point, there would be little to no movement-prohibitive contact between the clutch element 202 and the interior wall of the housing 102, thereby enabling the shaft 104 to slide or rotate within the housing 102.

Cam

In some embodiments, the device of the present invention features a cam 204. The cam 204 is in its rest position when the activator 106 is disengaged. When the cam 204 is in its rest position, it causes the clutch element 202 to be in contact with the interior wall of the housing 102. When activator 106 is engaged, the cam 204 moves longitudinally along the shaft 104 towards the distal end of shaft 104, thereby allowing the clutch element 202 to pivot around the pin 210.

Embodiments of the present invention include those in which the cam 204 is held in its rest position by a spring mechanism, by a magnet, by hydraulic pressure, or by using a compressible substance, such as rubber.

In some embodiments, the engagement of the activator 106 mechanically forces the cam 204 to move from its rest position. When the activator 106 is disengaged, the mechanical force that was holding the cam 204 in its rest position prior to the engagement of the activator 106 moves the cam 204 back to its rest position. Thus, by way of example only, the engagement of activator 106 moves the cam distally against a spring 206, thereby allowing the clutch element 202 to rotate freely about the pin 210. Once the activator 106 is disengaged, the spring 206 pushes the cam 204 towards the, proximal end of the shaft and thereby forces the clutch element 202 to move outward and come into contact with the interior wall of the housing 102.

In other embodiments, the activator 106 is a switch that turns an electrical current on or off. In certain embodiments the engagement of the activator 106 turns the electrical current on whereas in other embodiments, the engagement of the activator 106 turns the electrical current off.

In certain embodiments, the cam 204 is held in its resting position by an electromagnet. Engagement of the activator 106 reverses the electric current to the magnet, whereupon the cam 204 is pushed away from its resting position allowing the clutch element 202 to pivot around the pin 210. Disengagement the activator 106 restores the original current and brings the cam 204 back to its resting position. The electromagnet can be a solenoid, for example.

In other embodiments, once engaged, the electromagnet moves the cam 204 away from its resting position. Once the electromagnet is disengaged the cam is returned to its resting position by mechanical means, e.g., a spring or hydraulic pressure, etc.

Certain embodiments of the invention include those in which there is no cam 204 and the clutch element 202 pivots around the pin 210 by electrically induced forces, such as electromagnets.

Magnetic Clutch

In certain embodiments, the clutch element 202 does not exist. In these embodiments when the activator 106 is engaged either the shaft 104 or the housing 102, or both, are magnetic and, consequently, the shaft 104 does not slide or rotate within the housing 102. When the activator 106 is engaged, neither the shaft 104 nor the housing 102 is magnetic and the shaft 104 may rotate or slide freely within the housing 102.

In these embodiments, either the shaft 104 or the housing 102, or both, are equipped with an electromagnet that is connected by wire to an electrical power source, such as a battery or an AC source. When the activator 106 is engaged, electrical current flows to the electromagnet and it becomes magnetic. The magnetization of the electromagnet in turn magnetizes the shaft 104 or the housing 102. When one of the shaft 104 or the housing 102 becomes magnetized, it magnetically attracts the other to the extent that under normal operating conditions, i.e., the amount of force that a surgeon is willing to apply to a surgical tool during a surgical operation, the shaft 104 and the housing 102 do not become separated. They become immobilized with respect to each other.

When the activator 106 is disengaged, electrical current to the electromagnet is cut off and it no longer is magnetic. Once the electromagnet has become demagnetized, neither the shaft 104 nor the housing 102 are magnetic. At this point, the shaft 104 can slide or rotate through the housing 102. Thus, the surgeon can disengage the activator 106, adjust the position of the shaft 104 within the housing 102 to the desired position, then re-engage the activator 106, after which the shaft 104 remains in its new position indefinitely, or until the surgeon changes the position once again.

CONCLUSION

Thus, those of skill in the art will appreciate that the devices described herein provide a single hand-actuated clutch for coarse adjustment of the position of certain instruments, such as a laparoscopic surgical tool.

One skilled in the art will appreciate that these devices are and may be adapted to carry out the objects and obtain the ends and advantages mentioned, as well as those inherent therein. The methods, procedures, and devices described herein are presently representative of preferred embodiments and are exemplary and are not intended as limitations on the scope of the invention. Changes therein and other uses will occur to those skilled in the art which are encompassed within the spirit of the invention and are defined by the scope of the disclosure.

It will be apparent to one skilled in the art that varying substitutions and modifications may be made to the invention disclosed herein without departing from the scope and spirit of the invention.

Those skilled in the art recognize that the aspects and embodiments of the invention set forth herein may be practiced separate from each other or in conjunction with each other. Therefore, combinations of separate embodiments are within the scope of the invention as disclosed herein.

All patents and publications mentioned in the specification are indicative of the levels of those skilled in the art to which the invention pertains. All patents and publications are herein incorporated by reference to the same extent as if each individual publication was specifically and individually indicated to be incorporated by reference.

The invention illustratively described herein suitably may be practiced in the absence of any element or elements, limitation or limitations which is not specifically disclosed herein. The terms and expressions which have been employed are used as terms of description and not of limitation, and there is no intention that in the use of such terms and expressions indicates the exclusion of equivalents of the features shown and described or portions thereof. It is recognized that various modifications are possible within the scope of the invention disclosed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the disclosure.

What is claimed is:

1. A clutch for adjusting the position of an instrument, comprising:
    a housing having an interior wall defining a hollow interior;
    a shaft, said shaft being capable of moving axially and rotationally within said hollow interior of said housing;
    at least one clutch element connected with said shaft; and
    an activator;
        whereby when said activator is disengaged said clutch element is in contact with said interior wall of said housing, preventing the movement of said shaft relative to said housing, and
        when said activator is engaged, said clutch element is not in contact with said interior wall of said housing, allowing for the movement of said shaft relative to said housing;
    wherein said instrument is connected to said shaft, and said movement of said shaft relative to said housing moves at least a distal end of said instrument; and
    wherein said activator is adapted to permit single-handed operation of said clutch element and said shaft.

2. The clutch of claim 1, further comprising a lining covering said interior wall of said housing.

3. The clutch of claim 1, wherein said clutch element is mounted within said shaft.

4. The clutch of claim 1, wherein said activator is normally disengaged and said clutch element is normally in contact with said interior wall of said housing.

5. The clutch of claim 1, wherein said activator is a button.

6. The clutch of claim 1, wherein said activator is a lever.

7. The clutch of claim 1, wherein said activator is an electrically operated activator.

8. The clutch of claim 1, wherein the activator is engaged and said shaft is moved axially and/or rotationally within said hollow interior of said housing simultaneously and using the same hand of an operator.

9. The clutch of claim 4, further comprising a spring mechanism such that when said activator is disengaged, said spring mechanism causes said clutch element to be in contact with said interior wall of said housing.

10. The clutch of claim 1, further comprising a cam in contact with said activator and said at least one clutch element,
    whereby the engagement of said activator causes said cam to move longitudinally within said shaft, and
    the disengagement of said activator causes said cam to return to a rest position.

11. The clutch of claim 10, wherein in said rest position said cam causes said clutch element to be in contact with said interior wall of said housing.

12. The clutch of claim 10, wherein the engagement of said activator causes an electrical current to move said cam longitudinally within said shaft.

13. The clutch of claim 12, wherein the disengagement of said activator causes an electrical current to return said cam to a rest position.

14. The clutch of claim 12, wherein the disengagement of said activator causes a spring mechanism to return said cam to a rest position.

15. The clutch of claim 10, wherein the engagement of said activator mechanically causes said cam to move longitudinally within said shaft.

16. The clutch of claim 14, wherein the disengagement of said activator causes a spring mechanism to return said cam to a rest position.

17. The clutch of claim 1, wherein the movement of said shaft causes said clutch element and said activator to move as well.

18. The clutch of claim 1, wherein said housing is cylindrical.

19. The clutch of claim 1, wherein said contact between said clutch element and said interior wall of said housing is frictional contact.

20. The clutch of claim 1, wherein said instrument is a surgical device.

21. The clutch of claim 1, wherein said surgical device is a laparoscopic surgical tool.

* * * * *